(12) United States Patent
Shaffer

(10) Patent No.: US 6,289,328 B2
(45) Date of Patent: *Sep. 11, 2001

(54) CHEMICAL SENSOR PATTERN RECOGNITION SYSTEM AND METHOD USING A SELF-TRAINING NEURAL NETWORK CLASSIFIER WITH AUTOMATED OUTLIER DETECTION

(75) Inventor: Ronald E. Shaffer, Alexandria, VA (US)

(73) Assignee: The United States of America as represented by the Secretary of the Navy, Washington, DC (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/061,256

(22) Filed: Apr. 17, 1998

(51) Int. Cl.[7] .............................. G06E 1/00; G06F 15/18; G06G 7/00
(52) U.S. Cl. .................................. 706/20; 706/19; 706/21
(58) Field of Search ................................. 706/20, 21, 19

(56) References Cited

U.S. PATENT DOCUMENTS 5,596,681 * 1/1997 Tamura ................................. 706/25
6,004,267 * 12/1999 Tewari et al. ....................... 600/300

OTHER PUBLICATIONS

Zaknich, A.; "An Efficient Modified Probabilistic Neural Network Hardware Implementation for Zero Crossing Thresholded Binary Signals"; 1998, IEEE; pp. 256–261.*

Christodoulau et al, "A New Technique for the Classification and Decomposition of EMG Signals", IEEE Proceedings of ICNN, Dec. 1995.*

* cited by examiner

*Primary Examiner*—George B. Davis
(74) *Attorney, Agent, or Firm*—John J. Karasek; Charles J. Stockstil (57) ABSTRACT

A device and method for a pattern recognition system using a self-training neural network classifier with automated outlier detection for use in chemical sensor array systems. The pattern recognition system uses a Probabilistic Neural Network (PNN) training computer system to develop automated classification algorithms for field-portable chemical sensor array systems. The PNN training computer system uses a pattern extraction unit to determine pattern vectors for chemical analytes. These pattern vectors form the initial hidden layer of the PNN. The hidden layer of the PNN is reduced in size by a learning vector quantization (LVQ) classifier unit. The hidden layer neurons are further reduced in number by checking them against the pattern vectors and further eliminating dead neurons using a dead neuron elimination device. Using the remaining neurons in the hidden layer of the PNN, a global, σ value is calculated and a threshold rejection value is determined. The hidden layer, σ value and the threshold value are then downloaded into a PNN module for use in a chemical sensor field unit. Based on the threshold value, outliers seen in the real world environment may be rejected and a predicted chemical analyte identification with a measure of uncertainty will be provided to the user.

7 Claims, 6 Drawing Sheets

PRIOR ART

CHEMICAL SENSOR PATTERN RECOGNITION SYSTEM AND METHOD USING A SELF-TRAINING NEURAL NETWORK CLASSIFIER WITH AUTOMATED OUTLIER DETECTION

BACKGROUND OF THE INVENTION

1. Field of the Invention

The present invention relates to a system and method for self-training a neural network classifier with automated outlier detection. More particularly, the present invention relates to a chemical sensor pattern recognition system and method for detecting and identifying the presence of chemical agents using a self-training neural network classifier employing a probabilistic neural network with a built in outlier rejection algorithm and a mechanism to reduce the size of the probabilistic neural network.

2. Description of the Related Art

In the industrial and the military environments a need has existed for a mechanism to identify a wide variety of chemical substances on a real-time basis. These substances often include compounds which are extremely dangerous. In the industrial environment these substances may include known carcinogens and other toxins. In the military environment these substances would include blistering agents such as mustard gas and neurotoxins such as nerve gas. Therefore, it is critical for the safety of personal to quickly and accurately detect and alert employees and troops when such substances are present. Just as critical a function is the avoidance of issuing false alarms by any chemical detection apparatus.

Figure 1:
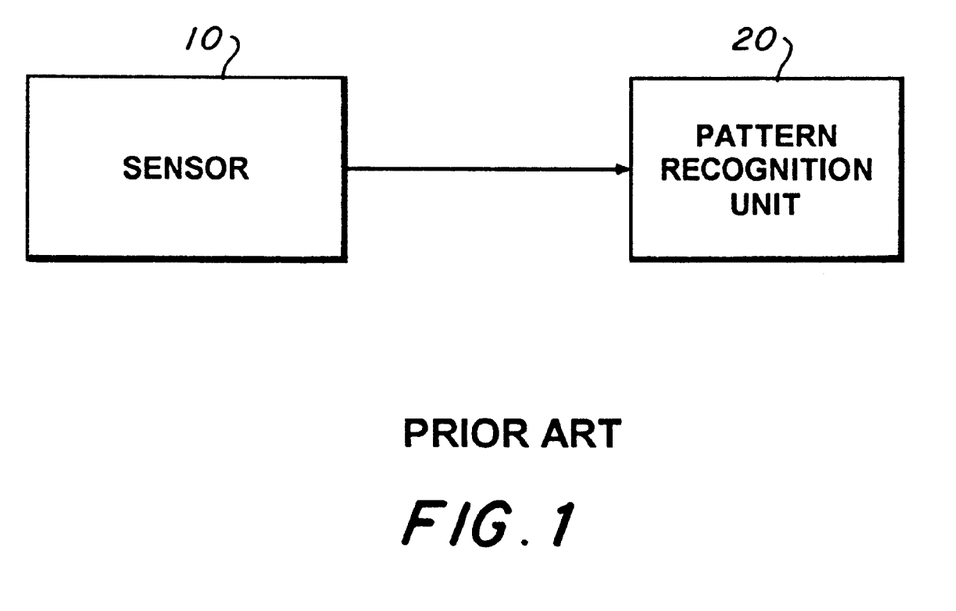
FIG. 1 is a diagram showing a configuration of chemical detection apparatus known in the prior art.

FIG. 1 is a diagram showing a configuration of a chemical detection apparatus known in the prior art which includes a sensor 10 and a pattern recognition unit 20. The pattern recognition unit 20 would include a computer system and software to analyze data received from the sensor 10 in order to identify the substance detected.

Referring to FIG. 1, traditional chemical detection methods have relied on the inherent selectivity of the sensor 10 to provide the pattern recognition unit 20 with the necessary information required to determine the presence or absence of target analytes. Advancements in chemical sensor technology have allowed the chemical detection apparatus shown in FIG. 1 to move from the laboratory to the field.

However, field measurements offer additional challenges not seen in laboratory or controlled environments. The detection of target analytes may be required in the presence of large concentrations of interfering species. The ideal chemical sensor 10 responds only to the targeted analyte(s). However, many sensor technologies, such as polymer-coated surface acoustic wave (SAW) chemical sensors, cannot achieve this measure of selectivity. Progress has been made and researchers have been able to overcome this potential drawback by utilizing arrays of partially selective sensors for sensor 10. Pattern recognition algorithms, in the pattern recognition unit 20, are then employed to interpret the sensor signals to provide an automated decision concerning the presence or absence of the targeted analyte(s). This approach has been employed successfully for semi-conducting gas oxide sensors, Taguchi gas sensors, MOSFET sensors, electrochemical sensors, and polymer-coated SAWs for the analysis of both liquid and gas phase species.

The underlying foundations for applying pattern recognition methods to chemical sensor arrays 10 are that the sensor signals numerically encode chemical information (i.e., a chemical signature) about the target analytes and the interfering species. In addition, pattern recognition methods assume that sufficient differences in the chemical signatures for the target analyte(s) and the interfering species exists for the methods to exploit, and that the differences remain consistent over time. For chemical sensor array pattern recognition, the responses for the number of sensors (represented by m) in the array form an m-dimensional vector ("vector pattern") in the data space. Recognition of the signature of the target compound(s) (analyte(s)) is based on the clustering of the patterns in the m-dimensional space. Analytes that have similar chemical features will cluster near each other in the data space, which allows them to be distinguished from other compounds mathematically.

Figure 2:
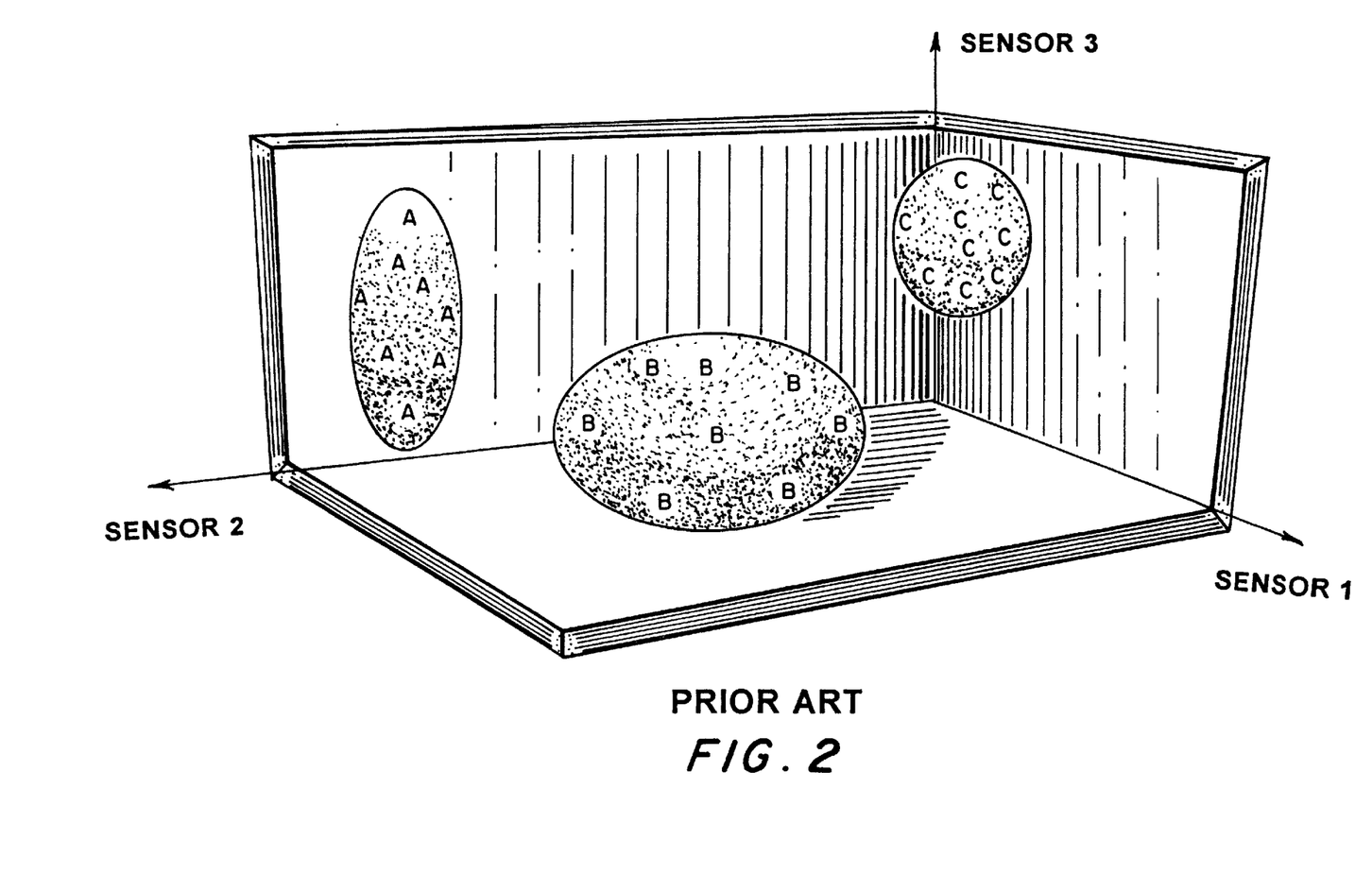
FIG. 2 is a diagram showing a pattern space comprising a three-sensor array (1, 2 and 3) and three classes of compounds (A, B, and C) used to form the pattern vectors in the prior art.

FIG. 2 is a diagram showing a pattern space comprising a sensor array with three sensors (1, 2, 3) and three chemical analytes (A, B, C). Since three sensors are used, the data space is a three dimensional data space. The three chemical analytes (A, B, C) form three different and easily distinguishable clusters of patterns (chemical signatures) in the three dimensional space. However, when attempting to detect chemicals in an environment outside the laboratory, frequently chemicals that closely chemically match the chemical to be identified are present. The closely related chemical is referred to as an interfering species and creates a pattern which partly overlaps with the cluster of the chemical to be detected.

In supervised pattern recognition methods, training patterns (i.e., chemical signatures) from known analytes and potential interfering species representative of the environment the sensors being deployed are used to develop classification rules by the pattern recognition unit 20. These classification rules are used to predict the classification of future sensor array data. The training patterns are obtained by exposing the sensor array to both the target analyte(s) and potential interfering analytes under a wide variety of conditions (e.g., varying concentrations and environments). The potential outcomes of the measurement (e.g., the presence or absence of the target analyte(s)) are considered the data classes. The number of data classes is application specific.

Supervised pattern recognition algorithms used in pattern recognition unit 20 are known in the art and used to analyze chemical sensor 10 array data. The two most popular pattern recognition approaches are linear discriminant analysis (LDA) and artificial neural networks (ANN). LDA is computationally simpler and easier to train than an ANN, but has trouble with multi-modal and overlapping class distributions. ANNs have become the de facto standard for chemical sensor pattern recognition due to the increasing power of personal computers and their inherent advantages in modeling complex data spaces.

The typical ANN for chemical sensor array pattern recognition uses the back-propagation (BP) method for learning the classification rules. The conventional ANN comprises of an input layer, one or two hidden layers, and an output layer of neurons. A neuron is simply a processing unit that outputs a linear or nonlinear transformation of its inputs (i.e., a weighted sum). For chemical sensor arrays, the neurons, as a group, serve to map the input pattern vectors to the desired outputs (data class). Using BP, the weights and biases associated with the neurons are modified to minimize the mapping error (i.e., the training set classification error). Upon repeated presentation of the training patterns to the ANN, the weights and biases of the neurons become stable and the ANN is said to be trained. The weights and biases for the neurons are then downloaded to the chemical sensor system for use in predicting the data classification of new sensor signals.

Despite their popularity, the BP-ANN methodology has at least five major disadvantages for application to chemical sensor arrays.

First, no known method exists for determining the optimal number of hidden layers and hidden layer neurons (i.e., the neural topology). This results in having to train many ANNs before finding one that is best for the application at hand.

Second, the iterative BP training algorithm is extremely slow, sometimes requiring several thousand presentations of the training patterns before convergence occurs. Other ANN training methods, such as Levenberg-Marquardt and Quick-Prop method, claim to achieve faster convergence, but their use is not widespread. Also, any learning algorithm based on incremental modifications to the weights and biases of the neurons runs the risk of falling prey to false minima and thereby requiring multiple training runs which further slow the process.

Third, the theoretical operation of how the ANN is able to map the inputs to the outputs is not clearly understood. There is no simple method of interrogating an ANN to discover why it classifies patterns correctly, or more importantly, why it fails to classify some patterns correctly.

Fourth, the outputs from a conventional ANN do not feature a statistical measure of certainty. For critical applications using chemical sensor arrays, the pattern recognition algorithm needs to produce some measure of confidence that it has correctly identified a particular classification. It is possible to obtain a confidence measurement by defining a probability density function comprising all possible outcomes of the ANN, but this method requires a large number of training patterns to be statistically valid and this further slows the training process.

Fifth, existing ANNs are unable to reject ambiguous or unfamiliar patterns (e.g., a compound that the ANN has not been trained to recognize), and thus misclassify them as being a member of the data class with which they are familiar. This often limits the applications of ANNs to controlled environments where all possible data classes are known in advance. Methods have been developed to overcome this problem by employing an ad hoc threshold to decide whether to accept or reject a new pattern. Another approach used to overcome this problem employs a dual ANN system where the first ANN decides whether to accept or reject the pattern and the second performs the actual classification. However, these solutions have not proven practical for application to chemical sensor arrays.

One variety of ANN which has been studied for application to chemical sensor array pattern recognition is the probabilistic neural network (PNN). For application to sensor arrays, PNNs overcome many of the disadvantages found with their more conventional counterparts discussed above. The PNN operates by defining a probability density function (PDF) for each data class based on the training data set and the optimized kernel width ($\sigma$) parameter. Each PDF is estimated by placing a Gaussian shaped kernel at the location of each pattern in the training set. A multivariate estimate of the underlying PDF for each class can be expressed as the sum of the individual Gaussian kernels. The PDF defines the boundaries (i.e., the classification rules) for each data class. The optimized kernel width ($\sigma$) parameter determines the amount of interpolation that occurs between data classes that lie near each other in the data space. For classifying new patterns, the PDF is used to estimate the probability that the new pattern belongs to each data class.

Figure 3:
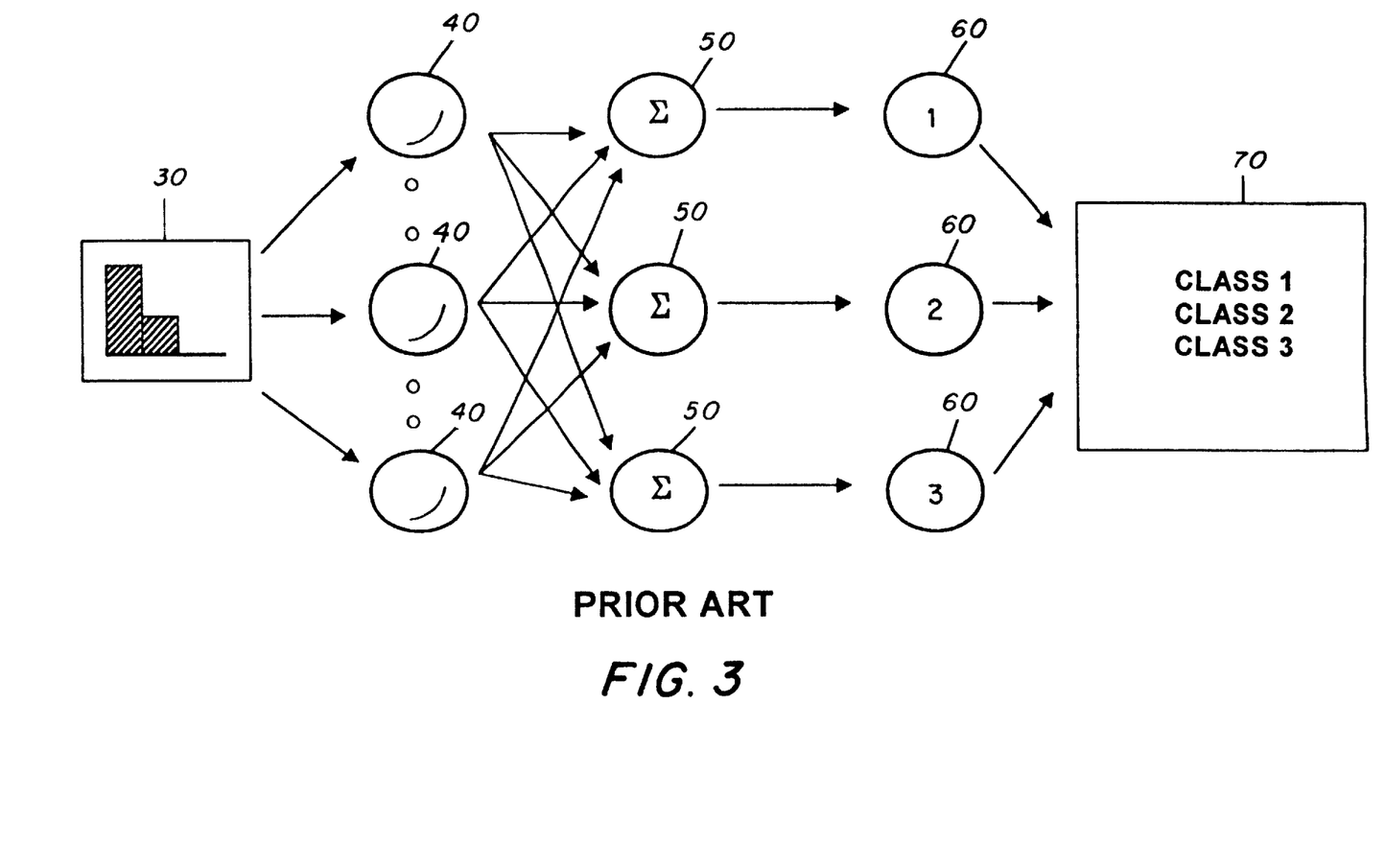
FIG. 3 is a diagram showing a probabilistic neural network (PNN) in which the inputs are the responses from the three-sensor array of FIG. 2, and the PNN outputs are the predicted classification for the given pattern in the prior art.

FIG. 3 is a diagram showing the topology of a probabilistic neural network (PNN) in which the inputs are the responses from the three-sensor array of FIG. 2, and the PNN outputs are the predicted classification for the given pattern in the prior art.

Referring to FIG. 3, PNN training is accomplished by simply copying each pattern in a training set (input layer) 30 to hidden layer neurons 40 and optimizing $\sigma$ for each neuron. Cross-validation and univariate optimization are most commonly employed to choose the best $\sigma$ for each neuron. The hidden layer neurons 40 and $\sigma$ values can then be downloaded to the chemical sensor array system for use in the field. The classification of new patterns is performed by propagating the pattern vector through the PNN. The input layer 30 is used to store the new pattern while it is serially passed through the hidden layer neurons 40. At each neuron in the hidden layer 40, the distance (either dot product or Euclidean distance) is computed between the new pattern and the input layer 30 pattern stored in that particular hidden neuron 40. The distance, d, is processed through a nonlinear transfer function as shown in equation 1.

$$output = \exp\left(-\frac{d}{\sigma^2}\right) \quad (1)$$

A summation layer 50 comprises of one neuron for each data class 70 and sums the outputs from all hidden neurons of each respective data class 70. The products of the summation layer 50 are forwarded to an output layer 60 (one neuron for each data class) and the estimated probability of the new pattern being a member of that data class 70 is computed. In the case of this example, since three chemical analytes (A, B, and C in FIG. 2) were supplied to the chemical detection apparatus (shown in FIG. 1) three different data classes 70 resulted from the PNN of FIG. 3.

Compared to conventional ANNs, the PNN offers extremely fast training times and provides mathematically sound confidence levels for each classification decision. However, the application of PNNs for chemical sensor array pattern recognition has been hindered by at least four major problems.

First, to predict the classification of new patterns, the distance between the new pattern and each pattern in the training set must be computed. For stand-alone sensor systems, the entire training set of patterns (i.e., the hidden layer) must be stored on board the microprocessor embedded in the sensor system. Since each and every training pattern must be stored, for many applications, this would require more memory than is available.

Second, as discussed above, the distance between the new pattern and each pattern in the training set (i.e., hidden layer) must be computed. For large training sets and sensor arrays, the number of calculations becomes prohibitive requiring more processing time than a real time application could permit. For certain applications, an embedded microprocessor could not process the sensor signals fast enough to operate in real-time without a significant reduction in the size of the hidden layer.

Third, a method is known in the art for detecting ambiguous patterns by setting a rejection threshold. If the outputs from the summation neuron for all classes are less than the rejection threshold, the new pattern is considered an outlier and no classification is performed. However, no generally accepted criteria for determining the best rejection threshold has ever been established. Setting an appropriate rejection threshold using the method described by Bartal et al. in "Nuclear Power Plant Transient Diagnostic Using Artificial Networks that Allow 'Don't-Know' Classifications" would require extensive experimentation or knowledge of the pattern space for each application.

Fourth, although PNN training is much faster than BP-ANN, the cross-validation and univariate optimization procedure (i.e., σ optimization) can be prone to local minima. Thus, several training runs must be performed to determine σ at the global-minimum training classification error.

Therefore, a need exists in the prior art for a pattern recognition system and method which is highly accurate, executes fast enough for real-time applications, is simple to train, has low memory requirements, is robust to outliers and thereby reduces the potential for false alarms, and provides a statistical confidence level for sensor patterns recognized.

SUMMARY OF THE INVENTION

An object of the present invention is to provide a device and method for self-training a neural network classifier with automated outlier detection for use in chemical sensor array systems.

The present invention has as a further object of providing a complete off-line software system for developing automated classification algorithms for field-portable chemical sensor array systems. To accomplish this objective the present invention includes a self-training algorithm for probabilistic neural networks (PNN) that dramatically reduces the memory and computational requirements, and a device and method for decreasing the probability that false alarms will occur through an automated outlier rejection scheme.

Objects and advantages of the present invention are achieved by a neural network pattern classifier using a probabilistic neural network. This device uses a dead neuron elimination unit to identify which neurons in a hidden layer of the probabilistic neural network are the nearest to a series of pattern vectors based on Euclidean distance and eliminates those neurons which have not been identified as nearest to any pattern vectors in the pattern vectors from the probabilistic neural network.

Further objects of the present invention are achieved by a neural network pattern classifier using a probabilistic neural network in which a σ optimization unit determines an optimal global σ value for all neurons in the probabilistic neural network. The optimal global σ value is computed from the summation of the dot product distance between each neuron and its nearest neighbor. Then a threshold determination unit calculates an outlier rejection threshold value based on the optimal global σ value.

Still further objects of the present invention are achieved by a neural network pattern classifier using a Monte Carlo simulation unit to generate a set of random pattern vectors, and a threshold determination unit to adjust an outlier threshold rejection value which rejects a predetermined percentage of the set of random patterns, wherein the outlier threshold rejection value is initially based on a global σ value.

Further objects and advantages of the present invention are achieved in accordance with embodiments by a PNN training computer system used to identify chemical analytes. This device uses a series of partially selective sensors to generate a set of sensory data when exposed to the chemical analytes. A pattern extraction unit connected to the partially selective sensors is used to extract a set of pattern vectors from the set of sensory data which form a set of initial hidden layer neurons of an initial probabilistic neural network. Then an LVQ classifier unit, connected to the pattern extraction unit, is used to reduce the number of neurons in the set of hidden layer neurons using learning vector quantization. Once the LVQ classifier completes processing, a dead neuron elimination unit connected to the LVQ classifier unit identifies neurons in the set of hidden layer neurons which have the shortest Euclidean distance to the pattern vectors and eliminates neurons in the set of hidden layer neurons which have not been identified as having the shortest Euclidean distance to any pattern vectors of the set of pattern vectors. A σ optimization unit connected to the dead neuron elimination unit then determines an optimal global σ value for all neurons in the probabilistic neural network. The optimal global σ value is computed from the summation of the dot product distances between each neuron and its nearest neighbor. A threshold determination unit connected to the σ optimization unit calculates an outlier rejection threshold value based on the optimal global σ value. Then a Monte Carlo simulation unit connected to the threshold determination unit generates a set of random pattern vectors using a Monte Carlo simulation. The threshold determination unit adjusts the outlier threshold value so that a predetermined percentage of the random pattern vectors are rejected as outliers.

Using the embodiments of the present invention described above and further detailed below, a self-training a neural network classifier may be quickly trained to identify chemical analytes detected by a chemical sensor array and to identify and reject analytes not seen during the training session as outliers.

BRIEF DESCRIPTION OF THE DRAWINGS

These and other objects and advantages of the invention will become apparent and more readily appreciated for the following description of the preferred embodiments, taken in conjunction with the accompanying drawings of which.

DESCRIPTION OF THE PREFERRED EMBODIMENTS

Reference will now be made in detail to the preferred embodiments of the present invention, examples of which are illustrated in the accompanying drawings, wherein like reference numerals refer to like elements throughout.

The present invention contains a complete set of algorithms designed to overcome the aforementioned problems encountered with the conventional ANN and PNN approaches to chemical sensor array pattern recognition. In the preferred embodiment, the present invention comprises a suite of MATLAB™ module files from Mathworks, Inc. and a Visual Basic™ subroutine. However, any suitable computer language may be used to implement the present invention. In the preferred embodiment, the user simply supplies the training patterns with known class identifications. The present invention uses a self-training (i.e., no user intervention necessary) PNN algorithm to automatically produce an optimally sized hidden layer and optimal global σ value. The optimal global σ value is the width associated with the Gaussian kernels which make up the PDF for each class of the summation layer 50 and the output layer 60, as previously discussed, and shown in FIG. 3. An outlier rejection threshold algorithm is then employed to develop an appropriate rejection threshold using the optimized PNN. The optimized PNN and the outlier rejection scheme can be downloaded to the ChemID plug-in module for use in a chemical sensor field unit. A detailed description will now be given of the algorithms in the present invention with reference the appropriate figures.

Sensory Input

Figure 4:
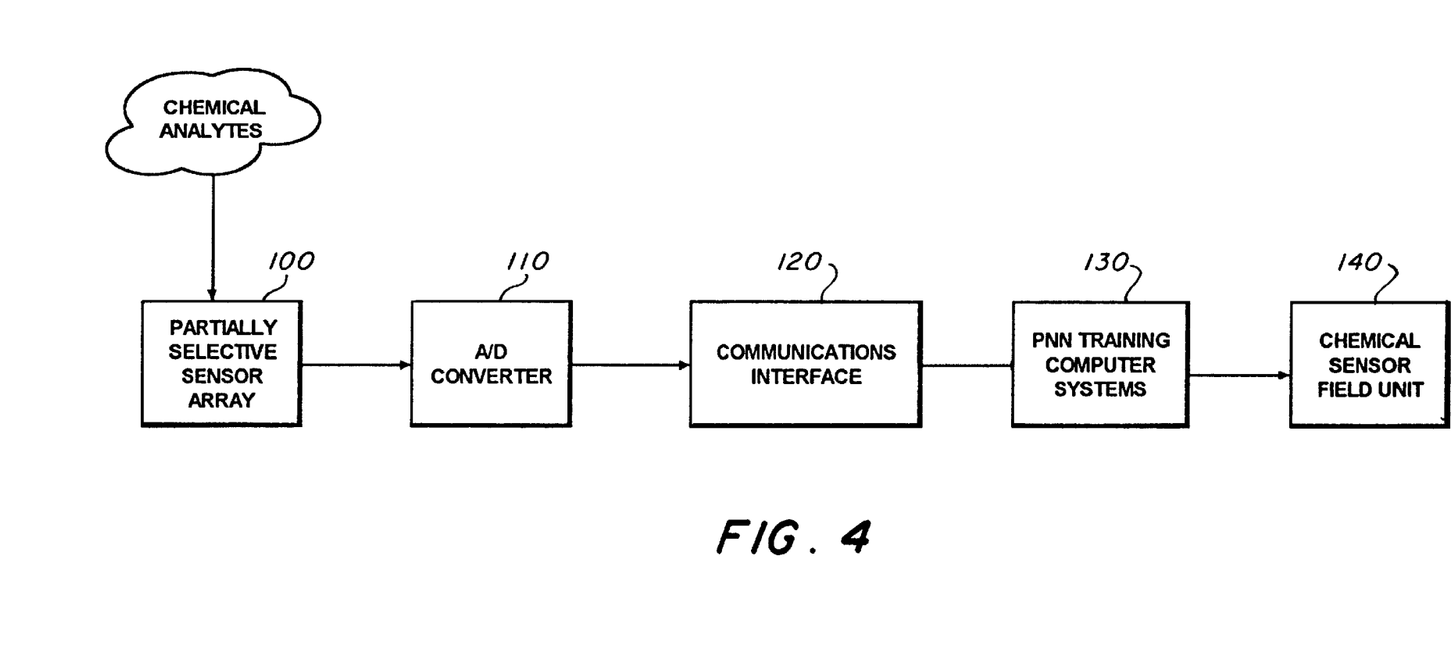
FIG. 4 is a diagram showing the overall hardware configuration of the present invention.

FIG. 4 is a diagram showing the overall hardware configuration of the present invention. The present invention includes: a partially selective sensor array 100; an A/D converter 110; communications interface 120; PNN training computer system 130; and a chemical sensor field unit 140.

Referring to FIG. 4, a training session for the present invention starts by exposing the partially selective sensor array 100 to one or more chemical analytes. The type of chemical sensors used are of a variety which are partially selective sensors. Examples of these types of partially selective chemical sensors include: polymer-coated surface acoustic wave (SAW) sensors; semi-conducting gas oxide sensors; Taguchi gas sensors; MOSFET sensors; and electrochemical sensors. In the presence of chemical analytes the partially selective sensor array 100 responds by generating an analog signal for each sensor.

Not only is the selection of the type of partially selective sensors 100 application driven, but so is the number of these sensors used in the present invention. In most applications of the present invention between ten and twenty partially selective sensors (i.e., a ten or twenty dimensional pattern vector) is the maximum number of sensors that are needed. However, in many applications, less than five sensors is all that is required to obtain the necessary chemical information (i.e., good clustering in multidimensional space). The desire to use the minimum number of sensors in a system is driven by the need to keep the instrumentation simple and reduce the size and cost of the system. The optimal number of sensors in the array is also determined by the specificity of the sensors themselves and the types of applications in which the sensors will be used.

The analog signals from the partially selective sensor array 100 are then passed through an analog to digital (A/D) converter 110 and transformed from an analog format to a digital format. The A/D converter 110 is connected to a communications interface 120 which can directly place the raw data from the partially selective sensors 100 into the memory of the PNN training computer system 130.

Pattern Extraction

Figure 5:
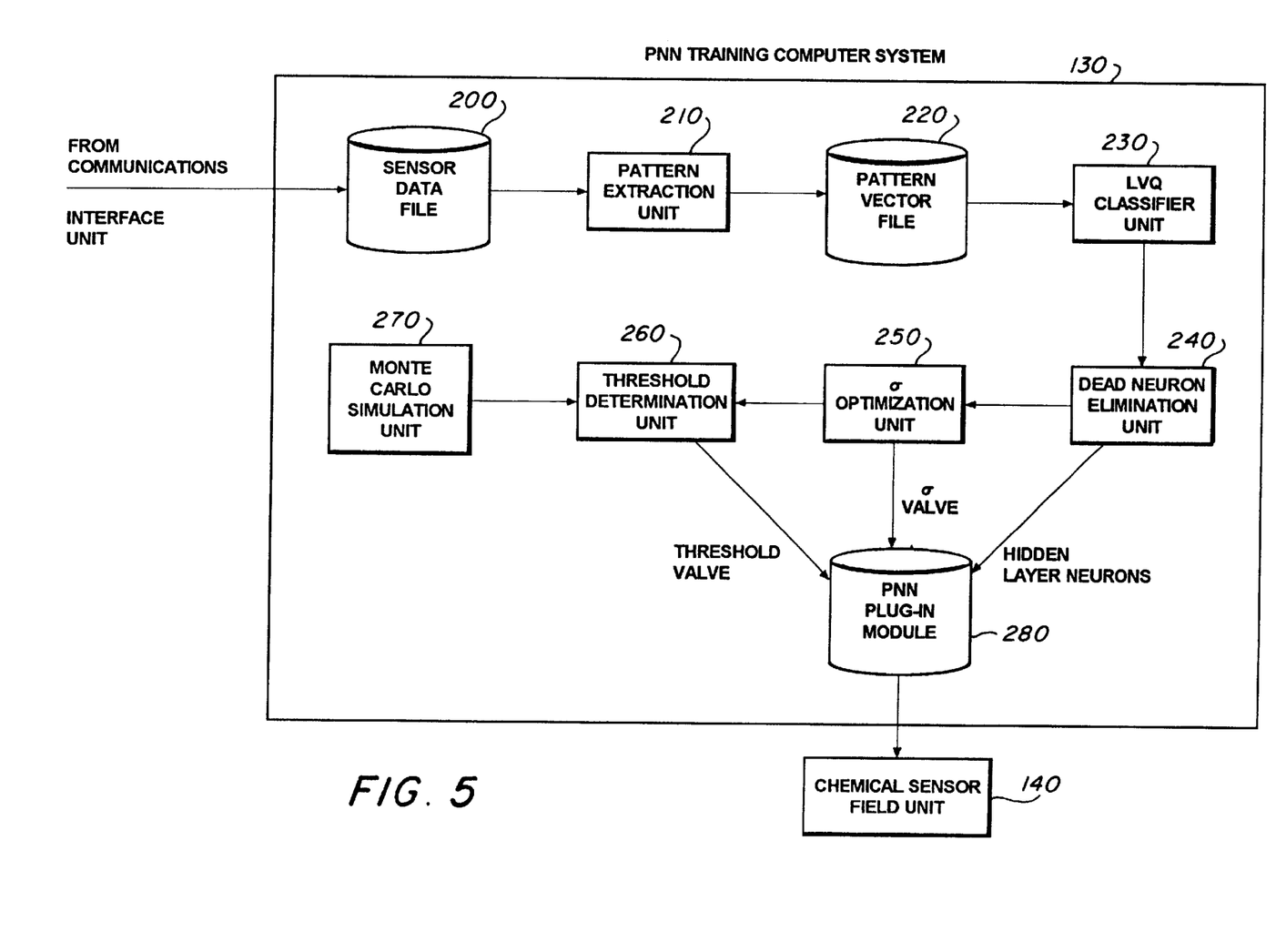
FIG. 5 is a diagram showing the configuration of the PNN training computer shown in FIG. 4 of the present invention.

FIG. 5 is a diagram showing the configuration of the PNN training computer 130 shown in FIG. 4 of the present invention. The PNN training computer 130 includes: a sensory data file 200; a pattern extraction unit 210; a pattern vector file 220; an LVQ classifier unit; a dead neuron elimination unit 240; a σ optimization unit 250; a threshold determination unit 260; a Monte Carlo simulation unit 270; and PNN Plug-In module 280. Once the PNN plug-in module 280 is created it can be placed in chemical sensor field unit 140.

Figure 6:
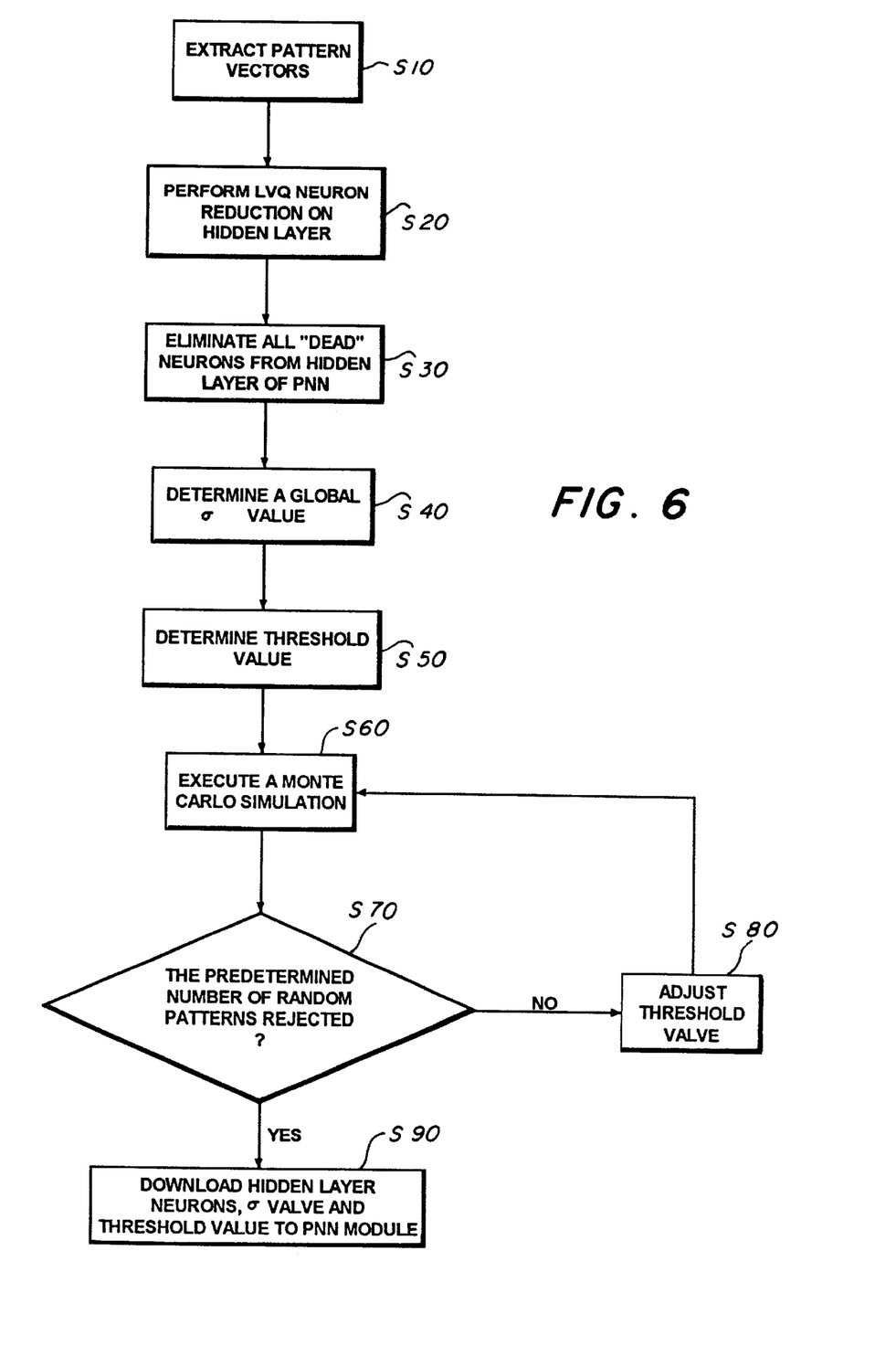
FIG. 6 is a diagram showing the process used in the present invention to generate the probabilistic neural network (PNN), global σ optimization and threshold value determination.

FIG. 6 is a diagram showing the process used in the present invention to generate the probabilistic neural network (PNN), global σ optimization and threshold value determination using the hardware configuration shown in FIG. 6. Both FIG. 5 and 6 will be referred to in the description of the present invention.

Referring to FIG. 5, once the raw sensor data is in the memory of the PNN training computer system 130, it can then be placed in a sensory data file 200 on a mass storage device as shown in FIG. 4. As shown in FIG. 5 and step S10 of FIG. 6, a pattern extraction unit 210 is provided which is an application specific module supplied by the user comprising software routines for converting raw sensor signals stored in the sensory data file into pattern vectors amenable for data analysis. A simple example of the pattern vectors created by three analytes using three sensors was previously discussed with reference to FIG. 1. A similar pattern extraction unit 210 is required in the field portable sensor unit for real-time analysis of the chemical analytes seen in the field.

In the PNN training computer system 130, the pattern vectors generated by the pattern extraction unit 210 form the initial training pattern 30 and hidden layer neurons (initial pattern vectors) 40, shown in FIG. 3, which will be used in generating the probabilistic neural network (PNN), described in detail later in this document. Once the extraction unit 130 places the pattern vectors into the hidden layer neurons 40 these hidden layer neurons may be thought of as initial hidden layer neurons 40 (or pattern vectors) and the initial PNN since they will undergo further processing to reduce their number.

Hidden Layer Reduction Using Learning Vector Quantization

Referring to FIG. 5, an LVQ classifier unit 230 is executed in step S20 of FIG. 6. Learning vector quantization (LVQ), originally developed by Kohonen and disclosed in an article entitled "Learning Vector Quantization for the Probabilistic Neural Network", is a competitive learning algorithm employed here to define a smaller set of pattern vectors that span the same space as the initial training pattern vectors stored in the pattern vector file. The resulting set of pattern vectors are substantially reduced in number from the original training pattern neurons and form the hidden layer of the PNN.

Using the LVQ classifier unit 230 shown in FIG. 5 and executed in step S20 of FIG. 6, the pattern vectors are considered hidden neurons and are forced to compete against each other to learn the structure of the pattern data space. The patterns in the training set are repeatedly presented many times (e.g., 10,000) to the LVQ classifier in random order. At each step, the neuron closest (based on Euclidean distance) to the current pattern vector (i.e., the "winning neuron") is moved toward the pattern if the classification for the winning neuron matches the classification of the pattern. Otherwise, if the classification for the winning neuron does not match the classification of the pattern vector, the neuron is moved away from the pattern. The distance that the winning neuron is moved is determined by the learning rate, which is slowly lowered over the course of training to decrease the likelihood of finding a local minima.

An important parameter for correct implementation of the LVQ classifier unit 230 executed in step S20 of FIG. 6 is the initial number of neurons (pattern vectors). Prior to the present invention this was determined by the user. To make the entire training operation autonomous, this user decision has been removed by initially employing a larger than necessary number of hidden neurons.

Once the LVQ classifier unit 230 completes processing in step S20 of FIG. 6, the number of neurons is substantially reduced and the size of the PNN is significantly smaller.

Hidden Layer Reduction Through Dead Neuron Elimination

Referring to FIG. 5, after the LVQ classifier unit 230 completes processing, the network structure is interrogated by passing each pattern in the training set through the hidden layer of the LVQ once and storing each winning neuron. The neurons in the hidden layer which never become a winning neuron are considered "dead neurons" and are removed from the hidden layer by a dead neuron elimination unit 240. This allows the hidden layer reduction step to proceed without user intervention and further decreases the size of the hidden layer to be passed to the PNN.

The identification and elimination of dead neurons by the dead neuron elimination unit 240 of FIG. 5 (executed in step S30 of FIG. 6) proceeds by creating a two dimensional array in which the columns represent the neurons after the LVQ classifier unit completes processing (from step S20 of FIG. 6) and the rows represent the initial pattern vectors from the pattern extraction unit (from step S10 of FIG. 6). In step S30 of FIG. 6, the distance between each pattern vector (row) and each neuron (column) is determined by Euclidean distance or other suitable metric. For each row (pattern vector), the neuron that was the closest (i.e., has the minimum distance) among the neurons in the hidden layer is flagged or a bit is set. All other columns along the row corresponding to the pattern vector are left unflagged or their bit set to zero. Once this is completed, the columns are checked to see if any of their rows had been flagged. Neurons that were flagged once or did not have at least one bit set (i.e., none of the rows in a column corresponding to the neuron) are not the closest neuron to any one pattern. These neurons are considered dead neurons and are eliminated from the hidden layer.

σ Optimization

Referring to FIG. 5 and executed in step S40 of FIG. 6, a σ optimization unit 250 begins execution immediately after hidden layer reduction by the LVQ classifier unit 240 and the dead neuron elimination unit 240 have completed processing. At this point in processing in the present invention, the hidden layer neurons have been reduced in number to a fraction of its original size seen after operation of the pattern extraction unit. PNN training proceeds by simply copying the hidden layer created by the LVQ classifier unit 230 and dead neuron elimination unit 240 (i.e., the winning neurons) to the hidden layer and performing a global or optimization. The PNN σ optimization unit 250 used in the PNN training computer system 130 employs a one-step calculation for σ optimization which results in a single global σ value for all neurons in the hidden layer. The calculation of the optimal global σ is based on computing the dot product distance between each neuron and its nearest neighbor as shown in equation 2 below.

$$\sigma_{opt} = 1.44 \sqrt{\frac{1}{n \cdot m} \sum_{j=1}^{n} \|\epsilon_j^* - \epsilon_j\|^2}, \quad (2)$$

In equation 2, m is the number of sensors in the array, n is the number of neurons in the hidden layer of the PNN, and $\epsilon_j^*$ represents the nearest neighbor of neurons $\epsilon_j$. The 1.44 term in Equation 2 is the correction factor that was found to work well with sensor array data. The basic assumption used in this approximation is that because the PDF for each class is estimated as the sum of the individual Gaussian kernels, the density estimate on a specific location in the pattern space is determined by the nearest kernel only. All other kernels are assumed to be so far away that their contribution to the density estimate is minimal. Thus, the approximation to the optimal kernel width (σ) should be based on the mean distance between nearest neighbors adjusted for the number of sensors and the number of neurons in the hidden layer.

This determination of the optimal global σ differs from that in the prior art by determining a single global σ for all neurons in the hidden layer and summation layer rather than determining σ on an individual neuron or class basis.

Outlier Rejection Threshold Determination

Referring to FIG. 5 and step S50 of FIG. 6, a threshold determination unit 260 determines the best outlier rejection threshold for a particular hidden layer and optimal global σ value using a Monte Carlo simulation. By default, the initial rejection threshold is set to $$r = \sigma_{opt}^4 \quad (3)$$

where r is the rejection threshold and $\sigma_{opt}$ was computed in equation 2. A large number (i.e., 10,000) random pattern vectors are presented to the PNN in the Monte Carlo simulation. The strength of the summation layer neurons 50 (see FIG. 2) are tested. If the aggregate score for the summation layer neurons 50 is less than r then the pattern is considered an outlier. Thus, that particular pattern is not similar to any of the patterns in the original training data set. A Monte Carlo simulation unit 270 shown in FIG. 5 and executed in step S60 of FIG. 6, generates a large series of random pattern vectors against which the computed threshold value may be tested. Under Monte Carlo simulation, the premise is that the PNN should reject somewhere between 80 and 90% of the randomly generated patterns. In step S70 of FIG. 6, if less than 80% (the predetermined number) of the random patterns are rejected then in step S80 of FIG. 6, r is increased by 20% and another Monte Carlo simulation is executed in step S60. If greater than 90% of the patterns are rejected, then r is reduced by 20% and in step S80 and another simulation is performed in step S60.

However, in the case where more sensitivity of the present invention to chemical analytes is important and there is less concern for possible false alarms, a rejection rate of random patterns as low as 50% may be used.

ChemID Plug-in Module

The optimized PNN hidden layer, σ, and r are downloaded to a PNN plug-in module 280 that can be read into a chemical sensor field unit 140, as shown in FIG. 4 and FIG. 5. As shown in FIG. 5 and processed in step S60 of FIG. 6, the PNN plug-in module 280 can be plugged into a chemical sensor field unit 140 which contains a copy of the pattern extraction unit 210 discussed above. Once the pattern extraction unit 210 determines the pattern vectors in the chemical sensor field unit 140, these pattern vectors are processed through the hidden layer of the PNN and those pattern vectors that exceed the threshold value r are rejected as outliers. Those pattern vectors that remain are presumed to match one of the neurons in the hidden layer and a classification decision with an associated confidence factor or measure of uncertainty is made based on the computed PDF of the PNN.

By utilizing the present invention described above, the problems encountered in the prior art can be overcome. As elaborated below, the user of the present invention will realize high accuracy in chemical analyte identification, fast execution speeds, a simple method of system training, low memory requirements, robust outlier rejection, and produce a measure of uncertainty.

High Accuracy

For application of the chemical sensor system to field measurements, the present invention provides a pattern recognition device and method with a low false alarm rate and few missed detections. In military applications such as the detection of toxic chemical vapors, classification accuracies of greater than 90% are realized by the present invention. The present invention accomplishes this through the use of a PNN in combination with a LVQ classifier unit, dead neuron elimination unit, σ optimization unit, and threshold determination unit.

Fast Execution Speed

The present invention is suitable for real-time analysis of chemical analytes by reducing the size of the PNN required and using a single global σ value as well as threshold value. Thus, the algorithms used in the present invention are less computationally intense than those seen in the prior art and execute faster.

Simple to Train

The classification rules used by the present invention are learned quickly by the use of a PNN. Using the present invention, the database of training patterns can be updated as needed in a quick and simple manner.

Low Memory Requirements

By reducing the number of neurons in the hidden layer using the LVQ classifier unit and the dead neuron elimination unit, the present invention creates a PNN which is a mere fraction the size seen in the prior art. Thereby, the PNN generated by the present invention is suitable for a field-portable sensor systems having a microcomputer with limited memory resources.

Robust to Outliers

As previously discussed, the environment in which chemical sensor arrays are used in the field is uncontrolled (e.g., battlefield). Therefore, a pattern recognition system must be able to differentiate between sensor signals on which It was trained and those on which it was not. The present invention accomplishes this by use of the σ optimization unit and threshold determination unit which determine the threshold value at which outliers should be rejected.

Produce a Measure of Uncertainty

The present invention is able to determine a statistical measure of uncertainty so that a confidence level of the classification can be determined. For sensor applications such as toxic vapor monitoring, such a measure aids in reducing the occurrence of false alarms by requiring that the sensor system be greater than 80% or 90% certain of a classification decision before a warning is given or an alarm sounded.

Although a few preferred embodiments of the present invention have been shown and described, it will be appreciated by those skilled in the art that changes may be made in these embodiments without departing from the principles and spirit of the invention, the scope of which is defined in the claims and their equivalents. In particular, reference has been made to the use of MATLAB™ module files from Mathworks, Inc. and a Visual Basic™ subroutine. However, it is also appreciated by a person of ordinary skill in the art that the present invention may be implemented in any computer language suitable to the task.

What is claimed is:

1. A method of pattern classification used for identifying chemical analytes using a probabilistic neural network, comprising the steps of:

comparing to determine a selection between a set of initial pattern vectors created by chemical analytes and contained in an initial hidden layer of an initial probabilistic neural network to a current set of neurons in a hidden layer of a probabilistic neural network obtained after processing said initial set of pattern vectors, said current set of neurons obtained by using a learning vector quantization procedure based on an Euclidean distance;

identifying which neurons of said current set of neurons are the nearest to each pattern vector of said set of initial patterns vectors; and eliminating from said probabilistic neural network those neurons of said current set of neurons which have not been identified as being nearest to any of said set of pattern vectors so that the remaining current set of neurons are selected to be used for pattern classification and so that said probabilistic neural network provides a corresponding output thereof for determination of said pattern classification for identifying chemical analytes.

2. A method of pattern classification using a probabilistic neural network comprising the steps of:

receiving sensory data from partially selective sensors to be used by a pattern extraction unit in generating pattern vectors;

comparing to determine a selection between a set of initial pattern vectors contained in an initial hidden layer of an initial probabilistic neural network to a set of current neurons in a hidden layer of a probabilistic neural network obtained after processing said pattern vectors, said current set of neurons obtained by using a learning vector quantization procedure based on an Euclidean distance;

identifying which neurons of said set of current neurons are the nearest to each pattern vector of said set of pattern vectors; and eliminating from said probabilistic neural network those neurons of said set of current neurons which have not been identified as being nearest to any of said set of pattern vectors so that the remaining set of current neurons are selected to be used for pattern classification and so that said probabilistic neural network provides a corresponding output thereof for determination of said pattern classification for identifying chemical analytes.

3. A method of pattern classification using a probabilistic neural network as recited in claim 2, wherein said partially selective sensors comprise one of the group consisting of semi-conducting gas oxide sensors, Taguchi gas sensors, MOSFET sensors, electrochemical sensors, and polymer-coated surface acoustic wave sensors.

4. A method of pattern classification used to identify chemical analytes comprising the steps of;

receiving a set of sensory data from a plurality of partially selective sensors;

extracting a set of pattern vectors from said set of sensory data which form a set of initial hidden layer neurons of an initial probabilistic neural network;

reducing the number of neurons in said set of initial hidden layer neurons through learning vector quantization to form a set of hidden layer neurons in said probabilistic neural network;

identifying neurons in said set of hidden layer neurons, already having been reduced by said reducing step, which have the shortest Euclidean distance to said set of extracted pattern vectors;

eliminating neurons in said set of hidden layer neurons of said identifying step which have not been identified as having the shortest Euclidean distance to said pattern vectors;

determining an optimal global $\sigma$ value for all neurons in said probabilistic neural network after said elimination of said neurons in said set of hidden layer neurons, wherein said optimal global $\sigma$ value is computed from the summation of dot product distances between each neuron and its nearest neighbor;

calculating an outlier rejection threshold value based on said optimal global $\sigma$ value;

generating a set of random pattern vectors using a Monte Carlo simulation; and adjusting said outlier threshold value so that a predetermined percentage of said random pattern vectors are rejected as outliers.

5. A neural network pattern classifier used for identifying chemical analytes using a probabilistic neural network comprising:

a plurality of partially selective sensors to generate sensory data in response to the presence of chemical analytes;

a pattern extraction unit to generate a plurality of pattern vectors using said sensory data;

a probabilistic neural network receiving said plurality of pattern vectors and forming them into an initial hidden layer of pattern vectors;

a dead neuron elimination unit receiving said initial hidden layer of pattern vectors and processing the initial hidden layer of pattern vectors to determine a current set of neurons and identifying which neurons in the current set of neurons are nearest to each pattern vector of said pattern vectors of said initial hidden layer, and eliminating those neurons of said current set of neurons that have not been identified as being nearest to any pattern vector of said pattern vectors of said initial hidden layer, so that the remaining set of neurons are selected to be used for pattern classification so that said dead neuron elimination unit provides a corresponding output thereof for determination of said pattern classification for identifying chemical analytes.

6. A neural network pattern classifier using a probabilistic neural network as recited in claim 15, wherein said plurality of partially selective sensors comprise one of the group consisting of semi-conducting gas oxide sensors, Taguchi gas sensors, MOSFET sensors, electrochemical sensors, and polymer-coated surface acoustic wave sensors.

7. A probabilistic neural network training computer system used to identify chemical analytes; comprising:

a plurality of partially selective sensors to generate a set of sensory data when exposed to said chemical analytes;

a pattern extraction unit connected to said plurality of partially selective sensors to extract a set of pattern vectors from said set of sensory data which form a set of hidden layer neurons of a probabilistic neural network;

a learning vector quantization classifier unit connected to said pattern extraction unit to reduce the number of neurons in said set of hidden layer neurons using learning vector quantization and to provide a corresponding output thereof;

a dead neuron elimination unit connected to receive said output of said learning vector quantization classifier unit to identify neurons in said set of hidden layer neurons which have the shortest Euclidean distance to said set of pattern vectors and eliminate neurons in said set of hidden layer neurons which have not been identified as having the shortest Euclidean distance to any pattern vectors of said set of pattern vectors, said dead neuron elimination unit providing an output representative of said set of hidden layer neurons having the shortest Euclidean distance;

a $\sigma$ optimization unit connected to receive said output of said dead neuron elimination unit and to determine an optimal global $\sigma$ value for all neurons in said probabilistic neural network, wherein said optimal global $\sigma$ value is computed from the summation of dot product distances between each neuron and its nearest neighbor and said $\sigma$ optimization unit provides a corresponding output;

a threshold determination unit connected to receive said output of said $\sigma$ optimization unit and to calculate an outlier rejection threshold value based on said optimal global $\sigma$ value and said threshold determination unit provides a corresponding output;

a Monte Carlo simulation unit connected to receive said output of said threshold determination unit and to generate a set of random pattern vectors using a Monte Carlo simulation; and said threshold determination unit in cooperation with said Monte Carlo simulation unit adjusting said outlier threshold value so that a predetermined percentage of said random pattern vectors rejected as outliers.

* * * * *